United States Patent [19]

Horzewski et al.

[11] Patent Number: 4,932,959

[45] Date of Patent: Jun. 12, 1990

[54] VASCULAR CATHETER WITH RELEASABLY SECURED GUIDEWIRE

[75] Inventors: Michael J. Horzewski; Ronald W. Songer, both of Sunnyvale, Calif.

[73] Assignee: Advanced Cardiovascular Systems, Inc., Mountain View, Calif.

[21] Appl. No.: 278,579

[22] Filed: Dec. 1, 1988

[51] Int. Cl.⁵ ............................................. A61M 25/00
[52] U.S. Cl. ..................................... 606/194; 604/96; 604/165
[58] Field of Search ................. 178/343, 344; 604/43, 604/169, 170, 95–103, 280; 606/192, 194

[56] References Cited

U.S. PATENT DOCUMENTS

| | | | |
|---|---|---|---|
| 2,819,718 | 1/1958 | Goldman | 604/96 |
| 4,004,588 | 1/1977 | Alexander | 604/96 |
| 4,166,468 | 9/1979 | Haynie | 604/256 X |
| 4,413,989 | 11/1983 | Schjeldahl | 604/96 |
| 4,580,573 | 4/1986 | Quinn | 604/256 X |
| 4,616,653 | 10/1986 | Samson et al. | 604/95 X |

Primary Examiner—Dalton L. Truluck
Attorney, Agent, or Firm—Fulwider, Patton, Lee & Utecht

[57] ABSTRACT

A vascular catheter having a central lumen adapted to slidably receive a guidewire therein with an inflatable collar or other suitable means to releasably secure or fix the guidewire within the lumen so that the catheter and guidewire can be advanced through a patient's vasculature as a unit. The catheter system is particularly suitable in balloon dilatation catheters for use in percutaneous transluminal coronary angioplasty procedures.

11 Claims, 1 Drawing Sheet

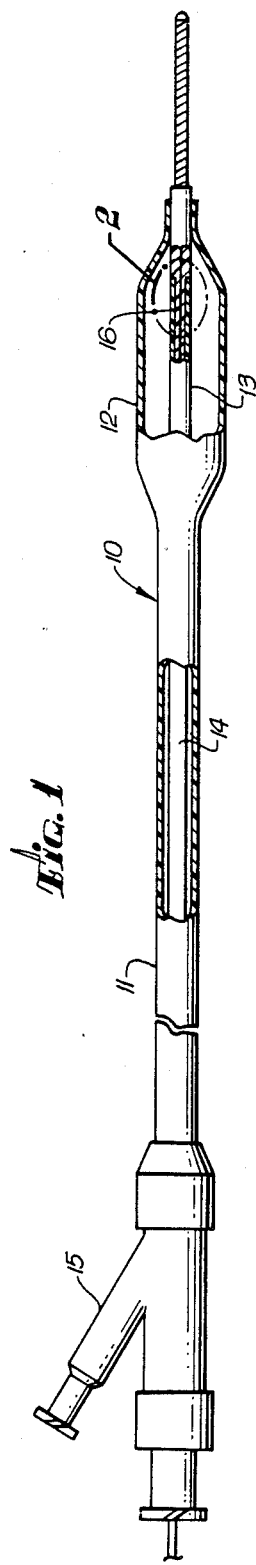
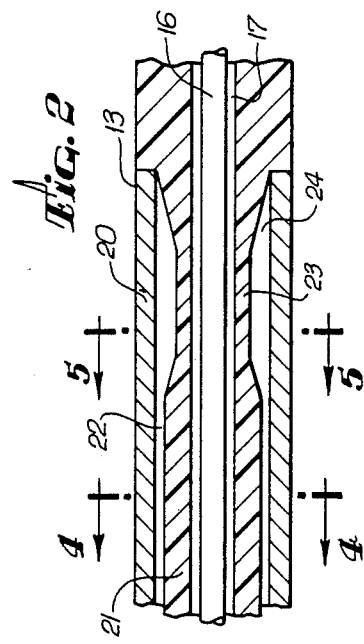
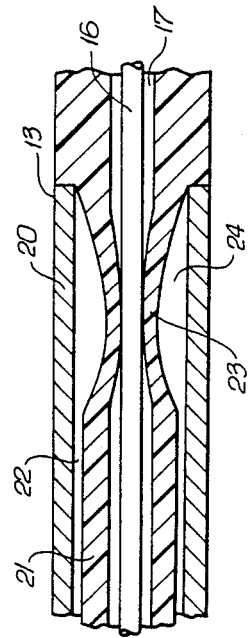
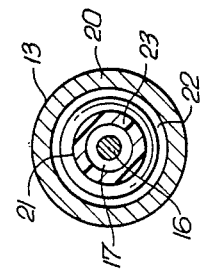
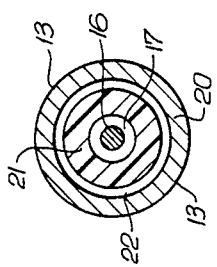

VASCULAR CATHETER WITH RELEASABLY SECURED GUIDEWIRE

BACKGROUND OF THE INVENTION

This invention generally relates to a vascular catheter assembly having a movable guidewire therein and particularly to such a catheter assembly which is suitable for percutaneous transluminal angioplasty procedures (PTCA).

In typical PTCA procedures, a guiding catheter is percutaneously introduced into the cardiovascular system of a patient through the brachial or femoral arteries and advanced therein until the preshaped distal tip of the guiding catheter is in the ostium of the desired coronary artery. A dilatation catheter having a balloon on the distal end thereof and a guidewire slidably disposed within an inner lumen thereof are introduced through the guiding catheter. The guidewire is first advanced through the distal tip of the guiding catheter into the patient's coronary vasculature until the distal end of the guidewire crosses the lesion to be dilated. Then the dilatation catheter is advanced over the previously introduced guidewire until the dilatation balloon on the distal extremity of the catheter is properly positioned across the lesion. Once in proper position across the lesion, the flexible, relatively inelastic balloon is inflated to a predetermined sized with radiopaque liquid at relatively high pressures (e.g , greater than 8 atmospheres) to radially compress the atherosclerotic plaque of the lesion against the inside of the artery wall to thereby dilate the lumen of the artery. After a short period (e.g. less than 30 seconds) the balloon is deflated so blood flow is resumed through the dilated artery and the dilatation catheter can be removed.

Further details of angioplasty procedures and the devices used in such procedures can be found in U.S. Pat. No. 4,332,254 (Lundquist); U.S. Pat. No. 4,323,071 (Simpson-Robert); U.S. Pat. No. 4,439,185 (Lundquist); U.S. Pat. No. 4,468,224 (Enzmann et al.) U.S. Pat. No. 4,516,972 (Samson); U.S. Pat. No. 4,538,622 (Samson et al.); U.S. Pat. No. 4,554,929 (Samson et al.); and U.S. Pat. No. 4,616,652 (Simpson) which are hereby incorporated herein in their entirety.

Steerable dilatation catheters with built-in or fixed guidewires or guiding elements are used with greater frequency because their deflated profiles are generally smaller than conventional dilatation catheters with movable guidewires having the same inflated balloon size. Moreover, the fixed guiding elements in the steerable dilatation catheters provide considerably greater pushability which allows them to cross much tighter lesions than dilatation catheters with movable guidewires. Further details of steerable dilatation catheters may be found in U.S. Pat. No. 4,582,181 (Samson), U.S. Pat. No. 4,619,263 (Frisbie et al.), U.S. Pat. No. 4,641,654 (Samson et al.), and U.S. Pat. No. 4,664,113 (Frisbie et al.) which are hereby incorporated in their entirety by reference thereto.

While the tubular members forming the catheter body utilizing a movable guidewire could be made from stiffer material or thicker walled tubing to increase the pushability of the catheter, such added stiffness would reduce the flexibility of the distal end of the catheter which allows the catheter to pass through the tortuous passageways of a patient's vascular system.

What has been needed and heretofore unavailable is a movable guidewire dilatation catheter system having increased stiffness to improve pushability without the loss of the distal flexibility necessary for the advancement thereof through a patient's vascular system. The present invention satisfies that need.

SUMMARY OF THE INVENTION

The present invention is directed to a movable catheter assembly having a movable guidewire therein characterized by improved pushability without attendant loss in flexibility, particularly in the distal portions thereof.

The catheter assembly in accordance with the present invention generally includes an elongated tubular member having an inner lumen extending along the length thereof which is adapted to slidably receive a movable guidewire therein. Disposed in the distal portion of the catheter assembly is means to releasably secure a guidewire disposed within the inner lumen of the tubular member so that the guidewire and catheter can be advanced as a unit through a patient's vasculature. The means to secure the guidewire is operable from the proximal end of the tubular member which extends out of the patient during angioplasty or other vascular procedures. By firmly but releasably securing the guidewire within the inner lumen of the tubular member, the entire catheter assembly can be readily advanced through a patient's vascular system even through tight stenotic regions. Once in place, the guidewire gripping means can be released so that the guidewire and the tubular member can then be moved independently of each other. In this manner, when the catheter cannot be advanced across a tight lesion once the guidewire has crossed the lesion, the gripping means can be actuated to fix the guidewire within the inner lumen so that the entire catheter assembly can be advanced forwardly thereby pushing the tubular member of the catheter assembly across the lesion. If the catheter is a dilatation catheter having an inflatable balloon on the distal end thereof, the catheter can be advanced so that the balloon crosses the lesion and can then be inflated to dilate the lesion.

In a presently preferred embodiment, the securing means is disposed in the distal portion of the tubular member of the catheter assembly which is provided with an inflatable inner member or collar disposed about the inner wall of the tubular member which defines the inner lumen. The inner member or collar expands inwardly when inflated to grip a guidewire disposed within the inner lumen to thereby fix the guidewire therein so that both the catheter and guidewire can be advanced as a single unit.

The tubular member generally comprises two separate tubular elements, an outer tubular element which is diametrically relatively rigid and an inner tubular element coaxially disposed therein having at least a portion thereof which is diametrically relatively flexible. The concentrically disposed tubular elements define an annular passageway for inflation fluids. When inflation fluid is directed through the annular passageway at elevated pressures, the relatively flexible portion of the inner tubular element expands inwardly toward the guidewire disposed within the inner lumen thereof to thereby grip or fix the guidewire therein in accordance with the present invention. The application of inflation fluid under pressure supplied through the annular passageway is controlled from the proximal end of the catheter which extends out of the patient.

By releasably securing the guidewire within the catheter body, the catheter body is further supported and thus has greater pushability so that it can be urged through tight lesions which could not otherwise be crossed by the unsupported catheter. Once the catheter guidewire assembly has crossed the lesion, the securing or gripping means can be released.

These and other advantages of the invention will become more apparent from the following detailed description thereof when taken in conjunction with the accompanying exemplary drawings.

BRIEF DESCRIPTION OF THE DRAWINGS

FIG. 1 is a side elevational view partially in section of a balloon dilatation catheter assembly embodying features of the invention;

FIG. 2 is a transverse cross-sectional view of the catheter assembly shown in FIG. 1 taken along the lines 2—2 and;

FIG. 3 is an enlarged side elevational view in section within the circle 3—3 of the catheter assembly shown in FIG. 1.

DETAILED DESCRIPTION OF THE INVENTION

FIGS. 1-3 generally illustrate a dilatation catheter assembly 10 embodying features of the invention which generally comprises an outer tubular member 11 having an inflatable balloon member 12 on the distal portion thereof, an inner tubular member 13 disposed within the outer tubular member 11 and defining therebetween a first annular passageway 14 for inflation fluid. A three-arm adapter 15 is provided on the distal portion of the catheter assembly 10. Guidewire 16 is disposed within the inner lumen 17 of the inner tubular member 13.

In accordance with a presently preferred embodiment, and as shown more clearly in FIGS. 2 and 3, the inner tubular member 13 generally comprises an outer tubular element 20 and an inner tubular element 21 concentrically disposed therein defining therebetween a second annular inflation lumen 22 which is in fluid communication with a source for inflation fluid at the proximal end of the dilatation catheter assembly 10.

The inner tubular element 21 is provided with a thin flexible section 23 which defines an inflation chamber 24. When inflation fluid under pressure from the second annular passageway 22 fills the inflation chamber 24, the thin flexible section 23 expands inwardly as shown in FIG. 3 to peripherally engage and thereby secure the guidewire 16. The outer tubular element 20 is diametrically relatively rigid in comparison with the inner tubular element 21 and thus generally is not deformed by the pressurized inflation fluid which expands the flexible section 23.

The outer tubular member 11 may be formed of suitable plastic material, such as polyethylene, polyvinylchloride, polyimide, polyester and the like which are conventional materials for dilatation catheters. The balloon member 12 is preferably formed of a relatively flexible but inelastic material such as irradiated polyethylene or polyethylene teraphthalate. For angioplasty procedures typical inflated balloon diameters may range from about 1 to about 4 mm. Preferably, the outer tubular element 20 of inner tubular member is longitudinally relatively flexible but diametrically relatively rigid and preferably formed from a material such as polyimide so that it does not significantly deform when inflation fluid is passed through annular passageway 22 between the inner and outer tubular elements of the inner tubular member 13. The inner tubular element 21 is preferably formed of a relatively flexible material such as polyethylene, polyester, or polyvinylchloride. The thinned inflatable section 23 readily collapses about the guidewire 16 when chamber 24 is filled with inflation fluid under pressure. The pressures required to fix the guidewire 16 within inner lumen 17 can vary depending upon the area of the thinned section which contacts the surface of the guidewire 16. Pressures up to 8 atmospheres have been found suitable. The inflatable section 23 is preferably located in the distal portion of the inner tubular member 13.

The outer surface of inner tubular element 21 can be formed from a tubular member with the outer portion thereof removed to provide the recess along a substantial length thereof which accepts the outer tubular element 20. The tubular element 20 can be secured in the recess by suitable adhesive, shrink-fit, or other suitable means. The inner tubular member 21 can also be formed from a resin-impregnated, wound fiber composite structure disclosed in copending application Ser. No. 241,047, filed 9-6-88 and entitled Composite Vascular Catheter. The composite structure may be formed by winding or braiding aramide fibers about a plastic tubular substrate (e.g., polyimide) and impregnating the would fibers with resin. Other methods can also be employed such as impregnating the fiber with resin prior to winding or braiding.

Typical dimensions of the outer tubular member 13 include an outer diameter of 0.03 inch (0.76 mm) and an inner diameter of 0.021 inch (0.53 mm). The outer tubular element 20 typically has an outer diameter of 0.03 inch and an inner diameter of 0.028 inch (0.71 mm). The collapsible section 23 of inner tubular element 21 may have an outer diameter of 0.025 inch (0.64 mm) and an inner diameter of 0.021 inch (0.53). The length of the collapsible section 23 can vary depending upon the inflation pressures. The more proximal section of inner tubular element 21 may have an outer diameter of 0.027 inch (0.69 mm) and an inner diameter of 0.21 inch.

While the present invention has been described herein primarily with respect to a balloon dilatation catheter, it should be apparent that the invention can be employed in a wide variety of vascular catheters which utilize a guidewire. Various modifications and improvements may be made without departing from the scope of the invention.

What is claimed is:

1. A dilatation catheter assembly for passage through an arterial passageway having a restriction therein, comprising an elongated catheter body with an inner lumen extending therethrough and an inflatable balloon on the distal portion thereof, a guidewire slidably disposed within the inner lumen having a flexible distal portion extending out the distal tip of the catheter body therein and means disposed in the inner lumen of the catheter body to releasably secure the therein so that the catheter assembly can be advanced as a unit through arterial restrictions.

2. The vascular catheter of claim 1 wherein the means to secure the guidewire within the inner lumen is an inflatable collar disposed about the interior of the distal portion of the first tubular member which expands inwardly when inflated.

3. The vascular catheter of claim 1 wherein the means to secure the guidewire within the inner lumen is operable from the proximal end of the catheter.

4. The vascular catheter of claim 2 wherein a conduit is provided which extends distally from the proximal end of the tubular member to the inflatable collar to direct inflation fluid thereto.

5. The vascular catheter of claim 4 wherein the tubular member has inner and outer tubular elements with an annular passageway leading to and in fluid communication with an inflation chamber of the inflatable collar.

6. The vascular catheter of claim 5 wherein the outer tubular element is diametrically relatively rigid and thereby less susceptible to deformation from pressurized inflation fluid which passes through the annular passageway between the inner and outer members than the inflatable inner collar which releasably secures the guidewire within the inner lumen.

7. The vascular catheter of claim 1 wherein a second elongated tubular member having an inflatable balloon on the distal portion thereof is concentrically disposed about the first tubular member and the distal end of the second tubular member is sealingly secured to the distal end of the first tubular member.

8. The vascular catheter of claim 7 wherein an annular passageway is defined between the first and second tubular members which is in fluid communication with the interior of the inflatable balloon on the distal portion of the second tubular member to facilitate the inflation thereof by means of inflation fluid.

9. A method of advancing a dilatation catheter assembly through the arterial system of a patient having a restriction therein, wherein the catheter assembly comprises a catheter body having distal and proximal portions with an inflatable balloon on the distal portion and a port in the distal end of the distal portion, an inner lumen extending along the interior of the catheter body and a guidewire slidable extending through the inner lumen with a flexible distal portion thereof extending out the port in the distal end of the catheter body, the method comprising advancing the guidewire within the patient's arterial system through a restriction therein, releasably securing the guidewire within the inner lumen by means therein and advancing the catheter assembly as a unit through the patient's arterial system so that the catheter body extends through the restriction.

10. The method of claim 9 wherein the inflatable balloon is disposed within the restriction, inflated, then removed therefrom.

11. The method of claim 9 wherein the guidewire is released.

* * * * *

UNITED STATES PATENT AND TRADEMARK OFFICE
CERTIFICATE OF CORRECTION

PATENT NO. : 4,932,959
DATED : June 12, 1990
INVENTOR(S) : Michael J. Horzewski and Ronald W. Songer It is certified that error appears in the above-identified patent and that said Letters Patent is hereby corrected as shown below:

Column 1, line 28 cancel "sized" insert --size--

Column 4, line 27 cancel "would" and insert --wound--.

Claim 1, line 58 after "the" and before "therein" insert --guidewire--.

Signed and Sealed this

Eighth Day of October, 1991

Attest:

HARRY F. MANBECK, JR.

*Attesting Officer*  *Commissioner of Patents and Trademarks*